(12) United States Patent
Bentley

(10) Patent No.: US 6,506,800 B2
(45) Date of Patent: Jan. 14, 2003

(54) 1,4 DIARYL-2,3-DIFLUORO-2-BUTENE INSECTICIDAL AND ACARICIDAL AGENTS

(75) Inventor: Terence James Bentley, East Windsor, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/950,860

(22) Filed: Sep. 12, 2001

(65) Prior Publication Data

US 2002/0058660 A1 May 16, 2002

Related U.S. Application Data

(60) Provisional application No. 60/231,996, filed on Sep. 12, 2000.

(51) Int. Cl.⁷ .......................... A01N 3/14; A01N 43/40; A01N 29/10
(52) U.S. Cl. ...................... 514/717; 514/277; 514/744; 570/129; 568/635
(58) Field of Search ................................ 514/277, 744, 514/715, 717; 504/352, 351, 209, 244; 568/639, 635, 637, 638; 570/129, 121, 122; 546/290, 303

(56) References Cited

U.S. PATENT DOCUMENTS

| 5,248,834 | A |   | 9/1993 | Elliott et al. ................. 528/638 |
| 5,763,700 | A |   | 6/1998 | Khambay et al. ............ 570/128 |
| 5,880,162 | A |   | 3/1999 | Khambay et al. ............ 514/683 |
| 5,892,131 | A | * | 4/1999 | Barnes et al. ................. 568/639 |
| 5,998,673 | A |   | 12/1999 | Barnes et al. ................. 568/634 |
| RE37,087  | E | * | 3/2001 | Franke et al. ................. 514/345 |
| 6,288,011 | B1 | * | 9/2001 | Bentley et al. ............... 504/352 |
| 6,342,642 | B1 | * | 1/2002 | Hu et al. ...................... 568/637 |

FOREIGN PATENT DOCUMENTS

| GB | 2 288 803 | 11/1995 |
| WO | WO 94/06741 | 3/1994 |
| WO | WO 97/16067 | 5/1997 |

* cited by examiner

Primary Examiner—Jean F. Vollano
(74) Attorney, Agent, or Firm—Keil & Weinkauf

(57) ABSTRACT

Pesticidal 1,4-diaryl-2,3-difluoro-2-butene compounds of formula I

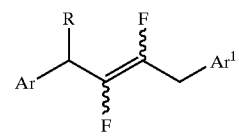

wherein
- Ar is phenyl, 1- or 2-naphthyl or a 5- or 6-membered heteroaromatic ring all of which aromatic systems may be optionally substituted;
- R is $C_2$–$C_6$-alkenyl, $C_4$–$C_6$-cycloalkenyl or $C_1$–$C_2$-alkoxy-$C_2$–$C_6$-alkyl; and
- $Ar^1$ is phenoxyphenyl, phenyl, biphenyl, phenoxypyridyl, benzylpyridyl, benzylphenyl, benzoylphenyl, 1- or 2-naphthyl, or a 5- or 6-membered heteroaromatic ring all of which aromatic systems may be optionally substituted, intermediates and methods for the preparation of compounds of formula I and compositions and methods comprising the compounds and compositions for the control of insect and acarid pests.

9 Claims, No Drawings

1,4 DIARYL-2,3-DIFLUORO-2-BUTENE INSECTICIDAL AND ACARICIDAL AGENTS

This application claims benefit of U.S. Provisional Application Ser. No. 60/231,996, filed Sep. 12, 2000.

DESCRIPTION

The present invention provides 1,4-diaryl-2,3-difluoro-2-butene compounds which are useful as insecticidal and acaricidal agents. The compounds are also useful for protecting plants from damage caused by insect and acarid attack and infestation.

1,4-diaryl-2,3-difluoro-2-butenes of the present invention have the structural formula I

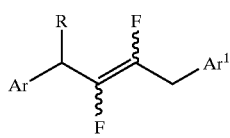

wherein

Ar is
  phenyl which is unsubstituted or substituted with any combination of from one to three halogen, $C_1$–$C_4$alkyl, $C_1$–$C_4$-haloalkyl, $C_1$–$C_4$-alkoxy, $C_1$–$C_4$-haloalkoxy or hydroxy groups,
  1- or 2-naphthyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, or
  a 5- or 6-membered heteroaromatic ring containing one to four nitrogen atoms or one to three nitrogen atoms and one sulfur atom or oxygen atom or one or two sulfur and/or oxygen atoms which is unsubstituted or substituted with any combination of from one to three halogen, $C_1$–$C_4$-alkyl, $C_1$–$C_4$haloalkyl, $C_1$–$C_4$-alkoxy or $C_1$–$C_4$-haloalkoxy groups;

R is $C_2$–$C_6$-alkenyl, $C_4$–$C_6$-cycloalkenyl or $C_1$–$C_2$-alkoxy-$C_2$–$C_6$-alkyl;

$Ar^1$ is
  phenoxyphenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups,
  phenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
  biphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
  phenoxypyridyl which is unsubstituted or substituted with any combination of from one to five halogen, $C_1$–$C_4$-alkyl, $C_1$–$C_4$-haloalkyl $C_1$–$C_4$-alkoxy or $C_1$–$C_4$-haloalkoxy groups,
  benzylpyridyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
  benzylphenyl which is unsubstituted or substituted with any combination of from one to five halogen, $C_1$–$C_4$-alkyl, is $C_1$–$C_4$-haloalkyl, $C_1$–$C_4$-alkoxy or $C_1$–$C_4$-haloalkoxy groups,
  benzoylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
  1- or 2-naphthyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, or
  a 5- or 6-membered heteroaromatic ring containing one to four nitrogen atoms or one to three nitrogen atoms and one sulfur atom or oxygen atom or one or two sulfur and/or oxygen atoms which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, and the optical isomers thereof, and
the (E)- and (Z)-isomers thereof.

This invention also provides intermediates and methods for the preparation of compounds of formula I, compositions containing the compounds, and methods for using the compounds and compositions.

U.S. Pat. No. 5,248,834 generically discloses certain 1-aryl-1-(3-aryl-1,2-difluoroprop-1-enyl)cyclopropane compounds.

EP-A 916 640 describes certain insecticidal and acaricidal 1,4-diaryl-2,3-difluoro-2-butenes, as well as methods for their preparation. Said application, however, does not disclose 1,4-diaryl-2,3-difluoro-2-butenes having alkoxy alkyl or alkenyl substituents in the 1-position.

The insecticidal and acaricidal activity of the compounds disclosed in the above-mentioned prior art in many cases is not fully satisfying.

It was, therefore, an object of the present invention to provide compounds which are more effective for the control of insect and acarid pests.

Accordingly, the 1,4-diaryl-2,3-difluoro-2-butene compounds of formula I have been found. Furthermore, intermediates and methods for the preparation of compounds of formula I as well as compositions containing them have been found.

The present invention also provides a method for the control of insect or acarid pests which comprises contacting said pests or their food supply, habitat or breeding grounds with a pesticidally effective amount of a compound of formula I.

The present invention also provides a method for the protection of growing plants from attack or infestation by insect or acarid pests which comprises applying to the foliage of the plants, or to the soil or water in which they are growing, a pesticidally effective amount of a compound of formula I.

In formula I above, 5- and 6-membered heteroaromatic rings containing one to four nitrogen atoms or one to three nitrogen atoms and one sulfur atom or oxygen atom or one or two sulfur and/or oxygen atoms include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each unsubstituted or substituted as described in formula I above.

Exemplary of halogen hereinabove are fluorine, chlorine, bromine and iodine;

The term "alkyl" is defined as a saturated, straight or branched chain hydrocarbon with 1 to 4 or 2 to 6 carbon atoms, such as methyl, ethyl, propyl, 1-methyl-ethyl, butyl, 1-methyl-propyl, 2-methyl-propyl, 1,1-dimethyl-propyl, pentyl, 1-methyl-butyl, 2-methyl-butyl, 3-methyl-butyl, 2,2-dimethyl-propyl, 1-ethyl-propyl, hexyl, 1,1-dimethylpropyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-tri-methyl-propyl, 1-ethyl-1-methyl-propyl und 1-ethyl-2-methyl-propyl;

The term "alkoxy" is defined as a saturated, straight or branched chain hydrocarbon with 1 to 2 or 4 carbon atoms (as described above) which is bond to the backbone via an oxygen (—O—) atom;

The term "cycloalkyl" is defined as a monocyclic, saturated hydrocarbon group with 3 to 6 carbon ring atoms, such as cyclopropyl, cyclobutyl, cyclopentyl, and cyclohexyl;

The term "haloalkyl" is defined as an alkyl group, as defined above, wherein the hydrogen atoms may be partially or totally substituted with halogen atoms as defined above, wherein the halogen atoms may be the same or different, for example $C_1$–$C_2$-haloalkyl such as chloro-methyl, bromomethyl, dichloro-methyl, trichloro-methyl, fluoro-methyl, difluoro-methyl, trifluoro-methyl, chloro-fluoro-methyl, dichlorofluoro-methyl, chloro-difluoro-methyl, 1-chloro-ethyl, 1-bromo-ethyl, 1-fluoro-ethyl, 2-fluoro-ethyl, 2,2-difluoro-ethyl, 2,2,2-trifluoro-ethyl, 2-chloro-2-fluoro-ethyl, 2-chloro-2,2-difluoro-ethyl, 2,2-dichloro-2-fluoro-ethyl, 2,2,2-trichloro-ethyl and pentafluoro-ethyl;

The term "haloalkoxy" is defined as an alkoxy group as defined above, wherein the hydrogen atoms may be partially or totally substituted with one or more halogen atoms as defined above, wherein the halogen atoms may be the same or different;

The term halocycloalkyl is defined as a cycloalkyl group as defined above, wherein the hydrogen atoms may be partially or totally substituted with one or more halogen atoms as defined above, wherein the halogen atoms may be the same or different;

The term "alkenyl" is defined as an unsaturated, straight or branched chain hydrocarbon with 2 to 6 carbon atoms and a double bond in an arbitrary position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3pentenyl, 3-methyl-3-pentenyl, 4-methyl-3-pentenyl, 1-methyl-4-pentenyl, 2-methyl-4-pentenyl 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1propenyl and 1-ethyl-2-methyl-2-propenyl.

The term "cycloalkenyl" is defined as an unsaturated, monocyclic hydrocarbon group with 4 to 6 carbon atoms with one double bond in an arbitrary position, such as cyclobutene, cyclopentene, and cyclohexene.

Wavy lines in structural formulae depict the carbon-carbon double bond in both the E- or the Z-isomeric configuration.

Preferred pesticidal agents of formula I are those wherein the variables have the following meanings, each alone or in combination:

Preferred are compounds of formula I wherein Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups.

More preferred are compounds of formula I wherein Ar is phenyl which is unsubstituted or substituted with any combination of from one to three halogen, preferably chlorine.

Most preferred are compounds of formula I wherein Ar is 4-chlorophenyl.

Also preferred are compounds of formula I wherein R is $C_2$–$C_4$-alkenyl or $C_1$–$C_2$-alkoxy-$C_2$–$C_6$-alkyl.

Especially preferred are compounds of formula I wherein R is $C_2$–$C_4$-alkenyl, preferably $C_2$–$C_3$-alkenyl.

Furthermore, especially preferred are compounds of formula I wherein R is $C_1$–$C_2$-alkoxy-$C_2$–$C_4$-alkyl, preferably $C_1$–$C_2$-alkoxy-$C_2$–$C_3$-alkyl.

Most preferred are compounds of formula I wherein R is 2-methoxyethyl, vinyl or allyl.

Moreover, compounds of formula I are preferred wherein $Ar^1$ is 3-phenoxyphenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups, 3-biphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or 3-benzylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups.

More preferred are compounds of formula I wherein $Ar^1$ is 3-phenoxy-phenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups.

Especially preferred are compounds of formula I wherein $Ar^1$ is 3-phenoxyphenyl which is unsubstituted or substituted with any combination of from one to six halogen, preferably fluorine.

Most preferred insecticidal and acaricidal compounds of formula I agents are those wherein Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;

R is $C_2$–$C_3$-alkenyl or $C_1$–$C_2$-alkoxy-$C_2$–$C_3$-alkyl; and $Ar^1$ is 3-phenoxyphenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups.

In a preferred embodiment of the present invention, the fluorine atoms attached to the carbon atoms of the double bond in the formula I compounds are in the (E)-configuration with respect to each other.

Formula I compounds of this invention which are particularly effective insecticidal agents include 1-[(2E)-4-(4-chlorophenyl)-2,3-difluoro-6-methoxy-2-hexenyl]-3-phenoxybenzene;

1[(2E)-4-(4-chlorophenyl)-2,3-difluoro-2,6-heptadienyl]-3-phenoxybenzene;

1-[(2E)-4-(4-chlorophenyl)-2,3-difluoro-2,5-hexadienyl]-3-phenoxybenzene; and

4-[(2E)-4-(4-chlorophenyl)-2,3-difluoro-6-methoxy-2-hexenyl]-1-fluoro-2-phenoxybenzene.

Compounds of formula I may be prepared as described in EP-A 916 640 and illustrated in Flow Diagram I, by reacting 1,1,2-trifluoro-1-propenes of formula II.1 with a defluorinating agent such as sodium bis(2-methoxyethoxy) aluminum hydride and a mineral acid such as hydrochloric acid to form 1,2-difluoro-1-propene compounds of formula II.2, and sequentially reacting such formula II.2 compounds with a base such as an alkyllithium base, preferably n-butyllithium, zinc chloride, tetra-kis(triphenylphosphine) palladium(0) and a substituted methyl halide of formula IV, wherein Z is halogen, preferably chlorine, bromine or iodine and $Ar^1$ is as defined for compounds of formula I above to afford compounds of formula I.

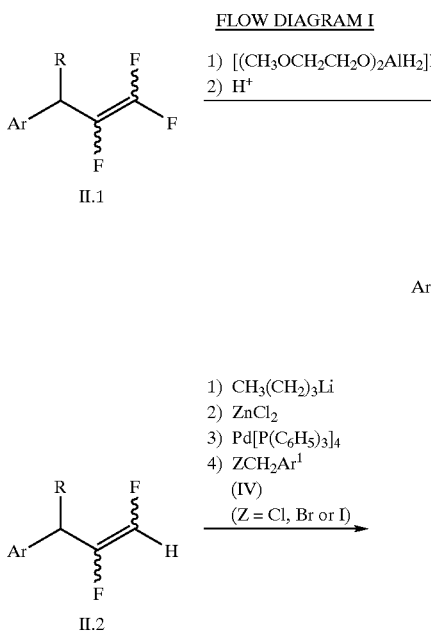

Compounds of formula II.1 may be prepared as described in J. Amer. Chem. Soc. (1986), 108, p. 4229 to 4230.

Alternatively, compounds of formula I wherein R is vinyl (Ia) or allyl (Ic) may be prepared from compounds of formula Ib, wherein R is 2-methoxyethyl, as depicted in Flow Diagrams II and III, respectively.

2-Methoxyethyl compounds of formula Ib, prepared by the method depicted in Flow Diagram I, are converted to alcohols of formula III.1 by treatment with a demethylating agent such as boron tribromide. Conversion of alcohols of formula III.1 to bromides of formula V with a brominating agent, preferably carbon tetrabromide/triphenylphosphine, and subsequent treatment with a salt of thiophenol, such as sodium thiophenoxide, affords thioethers of formula III.2. Oxidation of thioethers of formula III.2 with an oxidizing agent, perferably m-chloroperbenzoic acid (m-CPBA) yields sulfoxides of formula III.3, which on heating in a solvent with a boiling point of at least 100° C. (normal conditions), such as halogenated hydrocarbons, preferably ortho-dichlorobenzene, affords vinyl compounds of formula Ia. These transformations are depicted in Flow Diagram II.

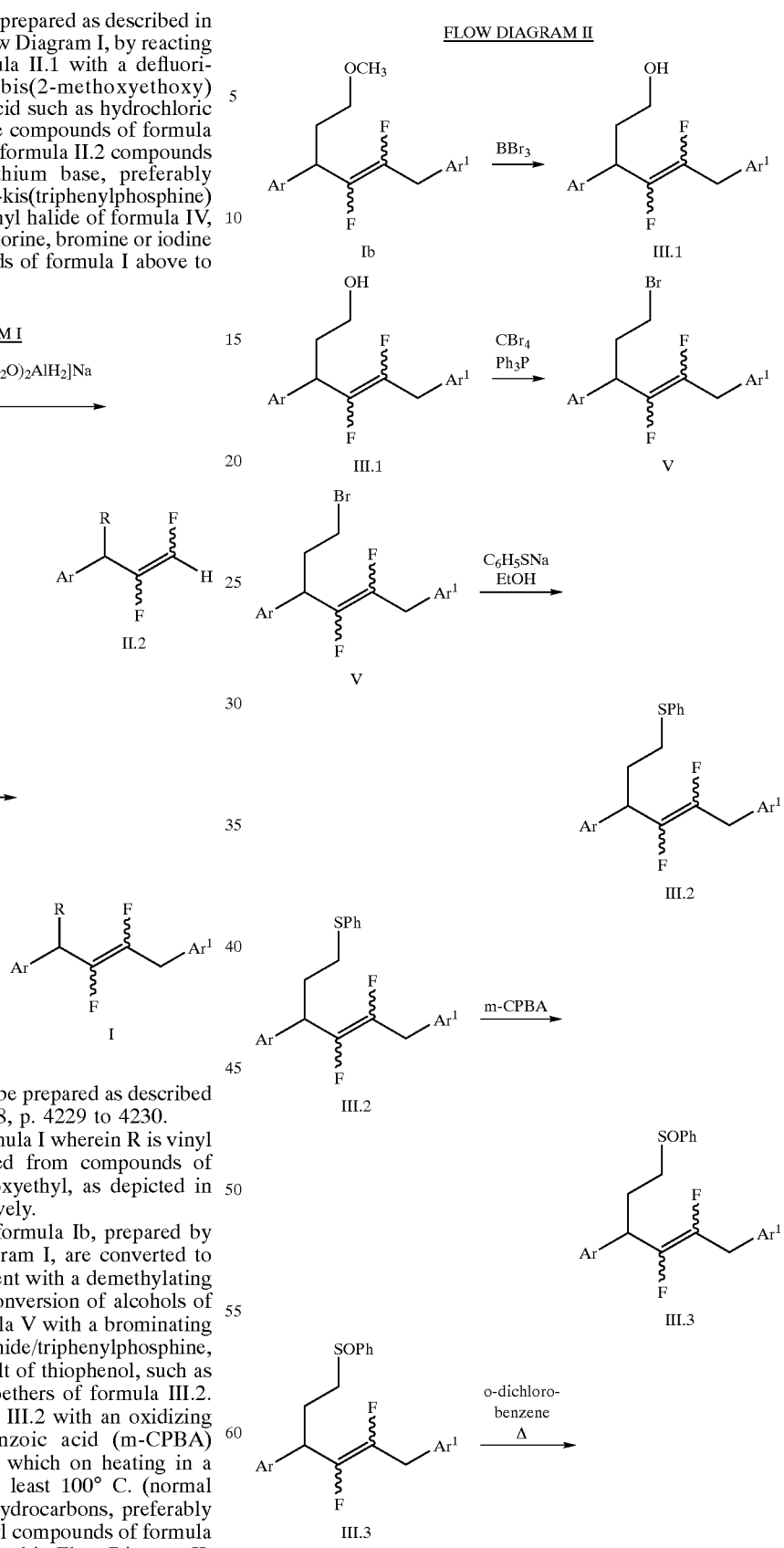

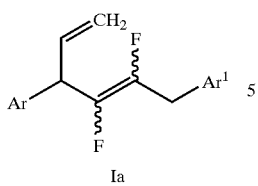

Ia

Allyl compounds of formula Ic are synthesized by the method depicted in Flow Diagram III. Alcohols of formula III.1 are treated with an oxidizing agent, such as pyridinium chlorochromate, and the resulting aldehydes of formula III.4 are treated with a silylating agent, such as trimethylsilylmethyl magnesium chloride, to afford compounds of formula III.5. Treatment of compounds of formula III.5 with an acid, such as acetic acid, affords allyl compounds of formula Ic.

FLOW DIAGRAM III

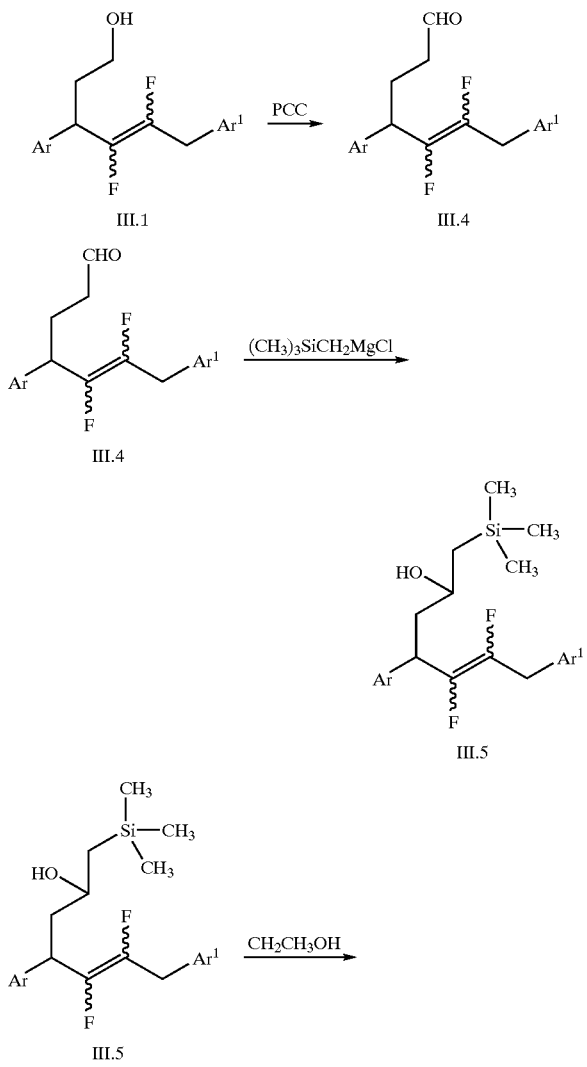

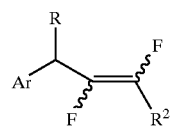

Ic

In a preferred embodiment of the present invention, the fluorine atoms attached to the carbon atoms of the double bond in the formula I compounds are in the (E)-configuration with respect to each other.

Compounds of formula I wherein the fluorine atoms at the double bond are in the (Z)-configuration may be prepared by isomerizing A certain intermediate compounds described hereinabove which are predominantly in the (E)-configuration using conventional procedures such as exposure to light.

The present invention provides intermediates of formula II,

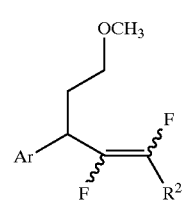

II wherein Ar and R are as defined as above for compounds of formula I, and $R^2$ is hydrogen or fluorine, for the preparation of compounds of formula I as depicted in flow diagram I, and the optical isomers thereof, and the (E)- and (Z)-isomers thereof.

Preferred are compounds of formula II wherein Ar and R are as preferred for compounds of formula I described above.

Particularly preferred are compounds of formula II.A

II.A wherein Ar is as defined for formula I and $R^2$ is hydrogen or fluorine, which are especially useful for the preparation of compounds of formula I wherein R is 2-methoxyethyl, vinyl, or allyl.

In a preferred embodiment of the present invention, the fluorine atoms attached to the carbon atoms of the double bond in compounds of formula II and II.A are in the (E)-configuration with respect to each other.

The present invention also provides intermediates of formula III,

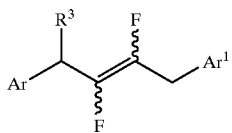

III wherein Ar and Ar¹ are defined as above for compounds of formula I and $R^3$ is phenylthio-$C_2$–$C_6$-alkyl, phenylsulfinyl-$C_2$–$C_6$-alkyl, hydroxy-$C_2$–$C_6$-alkyl, formyl-$C_2$–$C_5$-alkyl, or $C_2$–$C_6$-alkyl vicinally substituted with hydroxy and trimethylsilyl, and the optical isomers thereof, and the (E)- and (Z)-isomers thereof.

Intermediates of formula III are used in the preparation of compounds of formula I as depicted in flow diagrams II and III.

Preferred are compounds of formula III wherein Ar and Ar¹ are as preferred for compounds of formula I described above.

In a preferred embodiment of the present invention, the fluorine atoms attached to the carbon atoms of the double bond in the formula III compounds are in the (E)-configuration with respect to each other.

Compounds of formula I are effective for controlling insect and acarid pests. Those compounds are also effective for protecting growing or harvested crops from damage caused by insect and acarid attack and infestation.

Insects controlled by compounds of formula I include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; coleoptera such as boll weevils, colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites.

Compounds of formula I are especially useful for the control of tobacco budworms, southern armyworms and corn rootworms.

In practice generally 10 ppm to 10000 ppm and preferably 100 ppm to 5000 ppm of a formula I compound, dispersed in water or another liquid carrier, is effective when applied to plants or the soil in which the plants are growing to protect the plants from insect and acarid attack and infestation.

Compounds of formula I are also effective for controlling insect and acarid pests when applied to the foliage of plants and/or to the soil or water in which said plants are growing in sufficient amount to provide a rate of 0.1 kg/ha to 4.0 kg/ha of active ingredient.

While compounds of formula I are effective for controlling insect and acarid pests when employed alone, they may also be used in combination with other biological chemicals, including other insecticides and acaricides. For example, the compounds of formula I may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenyl ureas, pyrroles and the like.

Compounds of formula I may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of formula I (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation.

In order to facilitate a further understanding of the invention, the following examples are presented primarily for the purpose of illustrating more specific details thereof.

EXAMPLE 1

Preparation of 3-(4-chlorophenyl)propan-1-ol

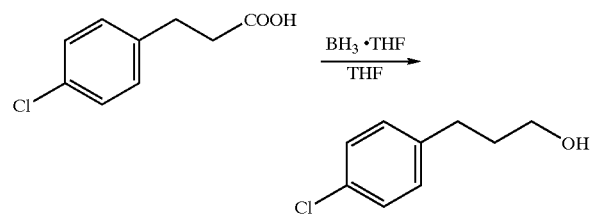

To a stirred solution of 3-(4-chlorophenyl)-propionic acid (10.0 g, 54.17 mmol) in tetrahydrofuran (100 ml) at −8° C. was added dropwise borane-tetrahydrofuran complex (100 ml, 1M in tetrahydrofuran, 100 mmol). The reaction mixture was cooled to 0° C. and methanol (100 ml) was added dropwise. The reaction mixture was warmed to room temperature, stirred for one hour and then concentrated in vacuo. The residue was treated with methanol (50 ml) and each time concentrated in vacuo twice to yield the title compound as an oil (9.61 g) which was characterized by IR spectral analysis and used without further purification.

EXAMPLE 2

Preparation of 3-(4-chlorophenyl)propyl methyl ether

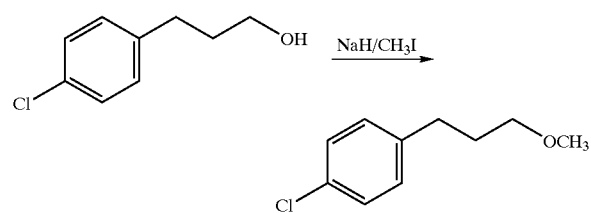

To a stirred solution of 3-(4-chlorophenyl)propanol (9.61 g, 54.17 mmol) and methyl iodide (7.0 ml, 112 mmol) in dry tetrahydrofuran (85 ml) under nitrogen was added 60% sodium hydride (2.83 g, 70.8 mmol) in portions. The reaction mixture was allowed to warm to room temperature and stirred overnight. The reaction mixture was treated with ice/water (150 ml), extracted with methylene chloride (3×250 ml), and the combined organic extracts were washed with water, dried over anhydrous sodium sulfate, and concentrated in vacuo. Chromatography of the residual yellow oil on silica gel eluting with hexane afforded the title compound as a yellow oil (8.69 g, 86% from 3-(4-chlorophenyl)propionic acid) which was characterized by NMR spectral analysis.

EXAMPLE 3

Preparation of 3-(4-chlorophenyl)-3-bromopropyl methyl ether

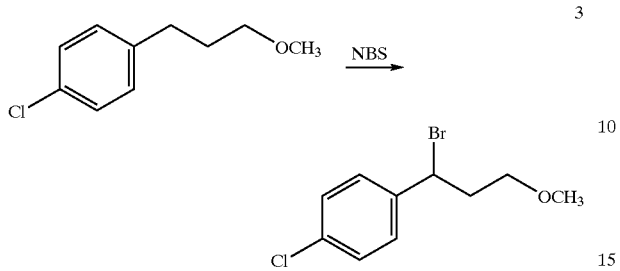

A mixture of 3-(4-chlorophenyl)propyl methyl ether (8.6 g, 46.5 mmol), N-bromosuccinimide (NBS; 9.43 g, 52.9 mmol), and a catalyst amount of 2,2'-azobisisobutyronitrile in ethylene dichloride (236 ml) was heated at 65° to 70° C. for three hours. The cooled reaction mixture was washed successively with water, saturated aqueous sodium bicarbonate and water, dried over anhydrous sodium sulfate and concentrated in vacuo to afford crude title compound (13.3 g) which was used without further purification.

EXAMPLE 4

Preparation of 1-Chloro-4-[2,3,3-trifluoro-1-(2-methoxyethyl)-2-propenyl]benzene

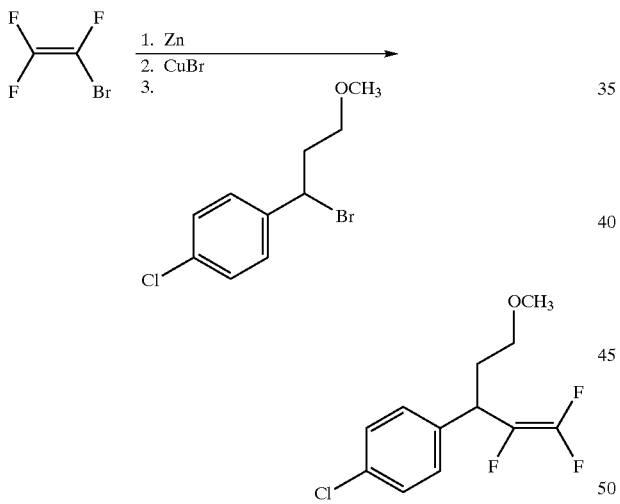

Bromotrifluoroethylene (41.5 g, 257 mmol) was distilled (dry ice condenser) into a flask containing zinc (13.6 g, 208 mmol) and N,N-dimethylformamide (153 ml), and the resulting mixture was heated at approximately 60° C. for two hours. The reaction mixture was purged with nitrogen for one hour, cooled to −8° C., treated with cuprous bromide (29.83 g, 208 mmol), and stirred for 30 minutes without external cooling. 3-(4-chlorophenyl)-3-bromopropyl methyl ether (17.06 g, 64.7 mmol) in N,N-dimethylformamide (10 ml) was added followed by limonene (5 drops), and the resulting mixture was heated at 50° C. for 8 hours. The cooled reaction mixture was quenched with aqueous ammonium chloride and thoroughly extracted with hexane. The combined organic extracts were dried over anhydrous sodium sulfate and concentrated in vacuo to a brown oil (10.76 g). Chromatography on silica gel eluting with methylene chloride:hexane (1:9) afforded the title compound as a yellow oil (2.25 g), which was characterized by IR, $^1$HNMR and mass spectral analysis.

EXAMPLE 5

Preparation of 1-Chloro-4-[(2E)-2,3-difluoro-1-(2-methoxyethyl)-2-propenyl]benzene

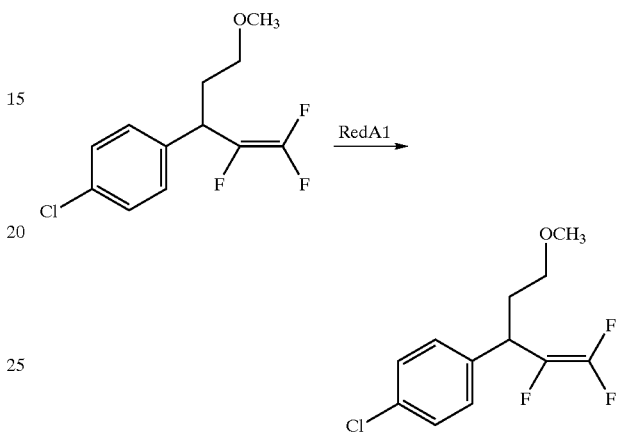

To a stirred solution of 1-chloro-4-[2,3,3-trifluoro-1-(2-methoxyethyl)-2-propenyl]benzene (2.25 g, 8.5 mmol) in tetrahydrofuran (56 ml) at −5° C. was added sodium bis(2-methoxyethoxy)aluminum hydride (RedAl, 6.7 ml of a 65% solution in toluene). The reaction mixture was allowed to warm to room temperature and stirred overnight. The reaction mixture was cooled to −5° C., and water (6.5 ml) was added dropwise with stirring, followed by 10% hydrochloric acid (30 ml). The resulting mixture was stirred for 45 minutes, diluted with water (50 ml) and extracted with methylene chloride (3×50 ml). The combined organic extracts were washed with water, saturated aqueous sodium bicarbonate, and water, dried over anhydrous sodium sulfate and concentrated in vacuo to afford the title compound as a brown oil (1.92 g) which was characterized by IR, $^1$HNMR and mass spectral analysis and used without further purification.

EXAMPLE 6

Preparation of 1-[(2E)-4-(4-Chlorophenyl)-2,3-difluoro-6-methoxy-2-hexenyl]-3-phenoxybenzene

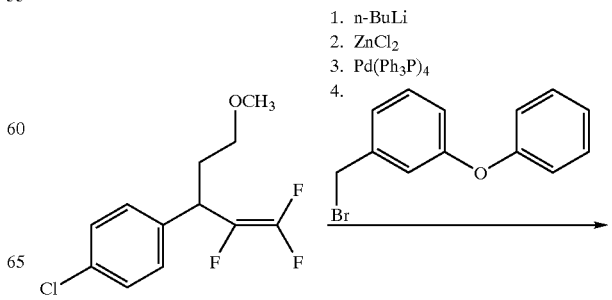

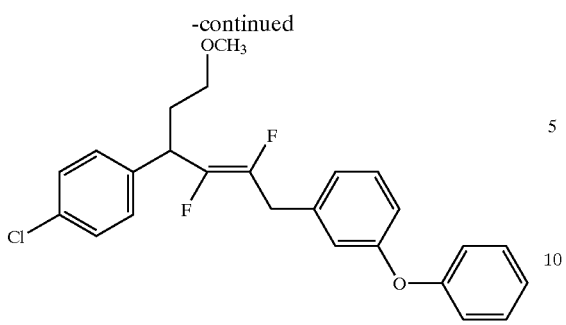

To a stirred solution of 1-chloro-4-[(2E)-2,3-difluoro-1-(2-methoxyethyl)-2-propenyl]benzene (0.87 g, 3.52 mmol) in tetrahydrofuran (10 ml) under nitrogen at −65° C. was added n-butyllithium (1.1 ml of a 2.5 M solution in hexane, 2.75 mmol). To this mixture was added zinc chloride (5.3 ml of 0.5 M in tetrahydrofuran, 2.65 mmol) and the resulting mixture was stirred for one hour. Tetrakis(triphenyl-phosphine)palladium (0.066 g, 0.057 mmol) in tetrahydrofuran (1 ml) was added, followed by α-bromo-3-phenoxytoluene (0.70 g, 2.66 mmol) in tetrahydrofuran (2 ml), and the resulting mixture was stirred and allowed to warm to room temperature over four hours and was then stirred for another sixteen hours. The reaction mixture was then quenched with water, diluted with 10% hydrochloric acid and thoroughly extracted with ethyl acetate. The combined organic extracts were dried over anhydrous sodium sulfate and concentrated in vacuo to a brown oil (1.378 g). Chromatography of this oil on silica gel eluting with ethyl acetate:hexane (5:95) afforded the title compound as a yellow syrup (0.359 g) which was characterized by IR, $^1$HNMR, $^{19}$FNMR and mass spectral analysis.

EXAMPLE 7

Preparation of 4-[(2E)-4-(4-chlorophenyl)-2,3-difluoro-6-methoxy-2-hexenyl]-1-fluoro-2-phenoxybenzene

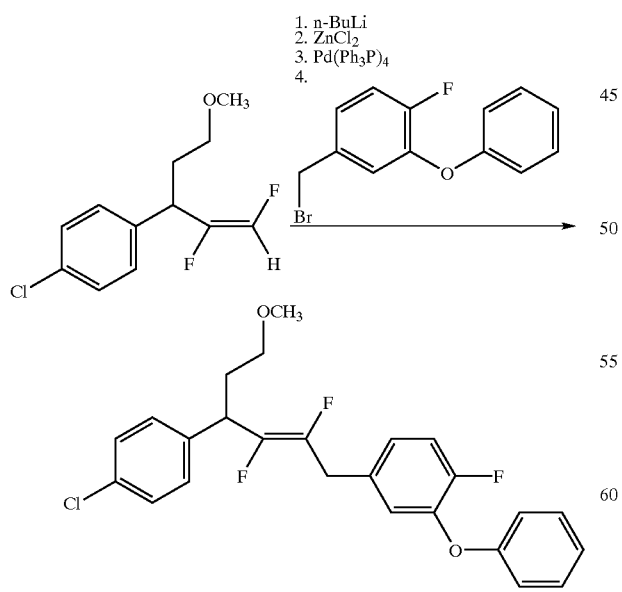

Using essentially the same procedure as described in example 6 with α-bromo-4-fluoro-3-phenoxytoluene afforded 4-[(2E)-4-(4-chlorophenyl)-2,3-difluoro-6-methoxy-2-hexenyl]-1-fluoro-2-phenoxybenzene as a pale yellow oil which was characterized by IR, $^1$HNMR and mass spectral analysis.

EXAMPLE 8

Preparation of (4E)-3-(4-Chlorophenyl)-4,5-difluoro-6-(3-phenoxyphenyl)-4-hexen-1-ol

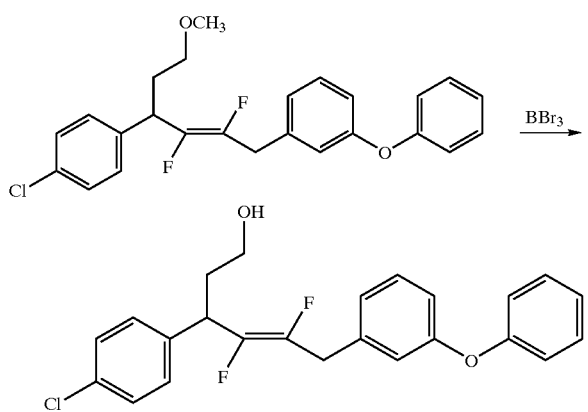

To a stirred solution of 1-[(2E)-4-(4-chlorophenyl)-2,3-difluoro-6-methoxy-2-hexenyl]-3-phenoxybenzene (0.081 g, 0.189 mmol) in methylene chloride at −5° C. under nitrogen was added dropwise boron tribromide (0.5 ml of a 1 M solution in methylene chloride, 0.5 mmol). The reaction mixture was allowed to warm to room temperature and stirred overnight at room temperature. The reaction mixture was cooled to −5° C., diluted with methanol (10 ml) and concentrated in vacua. The residue was taken up in methanol (10 ml) and the solution again concentrated. The residue was taken up in methylene chloride (25 ml), washed successively with water, saturated aqueous sodium bicarbonate and water, dried over anhydrous sodium sulfate and concentrated in vacuo to a brown gum. Chromatography of this gum on silica gel afforded the title compound as a tan syrup (0.057 g) which was characterized by $^1$HNMR, $^{19}$FNMR and mass spectral analysis.

EXAMPLE 9

Preparation of (4E)-3-(4-chlorophenyl)-4,5-difluoro-6-(4-fluoro-3-phenoxyphenyl)-4-hexen-1-ol

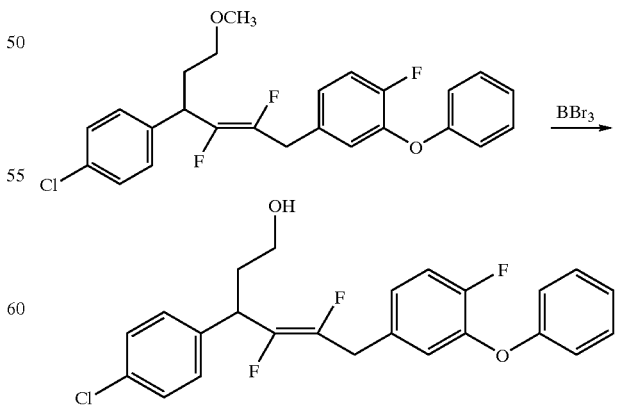

Using essentially the same procedure as described in example 8 on 4-[(2E)-4-(4-chlorophenyl)-2,3-difluoro-6- methoxy-2-hexenyl]-1-fluoro-2-phenoxybenzene afforded the title compound as a brown oil which was characterized by $^1$HNHR, $^{19}$FNMR and mass spectral analysis.

EXAMPLE 10

Preparation of 1-[(2E)-6-bromo-4-(4-chlorophenyl)-2,3-difluoro-2-hexenyl]-3-phenoxybenzene

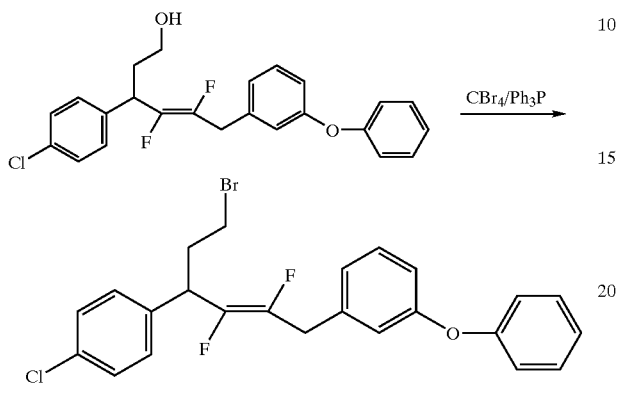

To a stirred solution of (4E)-3-(4-chlorophenyl)-4,5-difluoro-6-(3-phenoxyphenyl)-4-hexen-1-ol (0.10 g, 0.24 mmol) in ether (5 ml) under nitrogen was added carbon tetrabromide (0.085 g, 0.256 mmol), followed by triphenylphosphine (0.067 g, 0.255 mmol), and the resulting mixture was stirred overnight at room temperature. Additional quantities of carbon tetrabromide (0.17 g, 0.51 mmol) and triphenylphosphine (0.134 g, 0.51 mmol) were added, and the reaction mixture was stirred for five hours. The reaction mixture was concentrated in vacuo and the residue chromatographed on preparative thin layer silica gel plates, developing with methylene chloride to afford the title compound as a colorless oil (0.08 g) which was characterized by $^1$MMR, $^{19}$FNMR and mass spectral analysis.

EXAMPLE 11

Preparation of 4-[(2E)-6-bromo-4-(4-chlorophenyl)-2,3-difluoro-2-hexenyl]-1-fluoro-2-phenoxybenzene

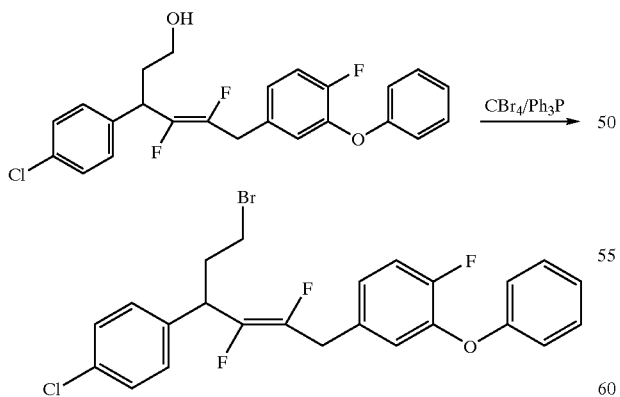

Using essentially the same procedure as described in example 10 on (4E)-3-(4-chlorophenyl)-4,5-difluoro-6-(4-fluoro-3-phenoxyphenyl)-4-hexen-1-ol afforded the title compound as a light tan syrup which was characterized by $^1$HNMR, $^{19}$FNMR and mass spectral analysis.

EXAMPLE 12

Preparation of (4E)-3-(4-chlorophenyl)-4,5-difluoro-6-(3-phenoxyphenyl)-4-hexenal

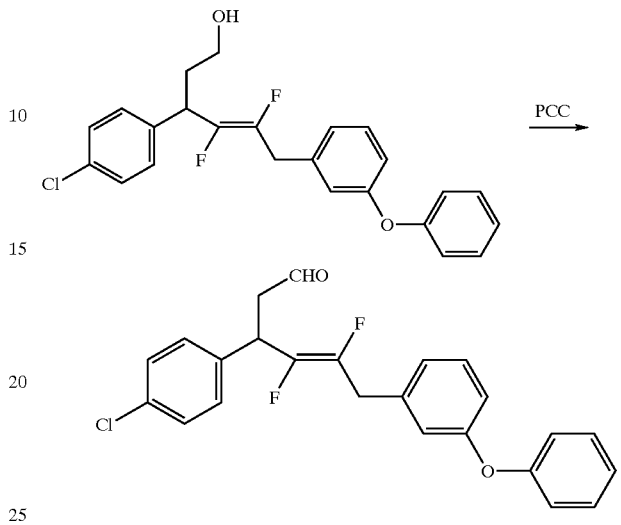

To a stirred solution of (4E)-3-(4-chlorophenyl)-4,5-difluoro-6-(3-phenoxyphenyl)-4-hexen-1-ol (0.332 g, 0.80 mmol) in methylene chloride (20 ml) at room temperature under nitrogen was added pyridinium chlorochromate (PCC; 0.268 g, 1.24 mmol), and the resulting mixture was stirred for four hours. The reaction mixture was diluted with methylene chloride, washed sequentially with 10% hydrochloric acid, water, saturated sodium bicarbonate and water, and dried over anhydrous sodium sulfate. Concentration in vacuo afforded the title compound as a brown oil (0.324 g) which was characterized by $^1$HNMR, $^{19}$FNMR and mass spectral analysis, and used without further purification.

EXAMPLE 13

Preparation of (5E)-4-(4-chlorophenyl)-5,6-difluoro-7-(3-phenoxyphenyl)-1-(trimethylsilyl)-5-hepten-2-ol

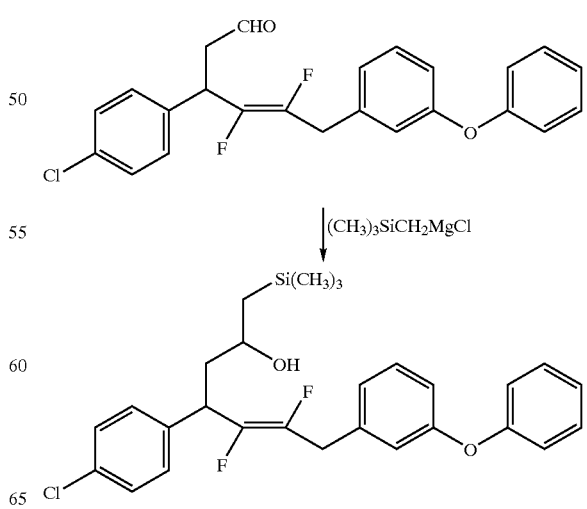

To a stirred solution of (4E)-3-(4-chlorophenyl)-4,5-difluoro-6-(3-phanoxyphenyl)-4-hexanal (0.324 g, 0.784 mmol) in ether (7.5 ml) under nitrogen at −8° C. was added dropwise trimethylsilylmethylmagnesium chloride (0.9 ml of a 1 M solution in ether, 0.9 mmol), The reaction mixture was allowed to warm to room temperature and stirred overnight. The reaction mixture was diluted with ether (5 ml), water (5 ml) was added followed by 10% hydrochloric acid until the reaction mixture was acidic. The mixture was then stirred for one hour, diluted with water (25 ml) and extracted with methylene chloride (3×25 ml). The combined organic extracts were washed sequentially with water, saturated sodium bicarbonate and water, dried over anhydrous sodium sulfate and concentrated in vacuo to a yellow oil (0.323 g). Chromatography of this oil on a preparative thin layer silica gel plate developing with methylene chlorideshexane (1:1) afforded the title compound as a colorless oil (0.194 g) which was characterized by IR, $^1$HNMR, $^{19}$FNMR and mass spectral analysis.

EXAMPLE 14

Preparation of 1-[(2E)-4-(4-chlorophenyl)-2,3-difluoro-2,6-hepta-dienyl]-3-phenoxybenzene

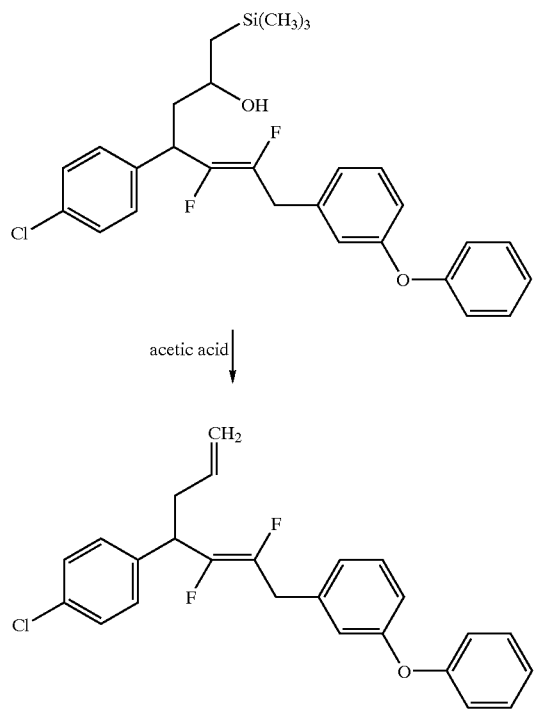

(5E)-4-(4-chlorophenyl)-5,6-difluoro-7-(3-phenoxyphenyl)-1-(trimethylsilyl)-5-hepten-2-ol (0.194 g, 0.39 mmol) was dissolved in glacial acetic acid (8 ml) containing water (40 drops) and heated at 105° C. to 110° C. for six hours. The reaction mixture was concentrated in vacuo, the residue diluted with saturated aqueous sodium bicarbonate, and extracted with methylene chloride (3×25 ml). The combined organic extracts were washed with water (25 ml), dried over anhydrous sodium sulfate and concentrated in vacuo to a yellow oil (0.16 g). Chromatography an a preparative thin layer silica gel plate developing with methylene chloride:hexane (1:1) afforded the title compound as a colorless oil (0.151 g) which is characterized by IR, $^1$HNMR and mass spectral analysis.

EXAMPLE 15

Preparation of 1-[(2E)-4-(4-chlorophenyl)-2,3-difluoro-6-(phenylsulfanyl)-2-hexenyl]-3-phenoxybenzene

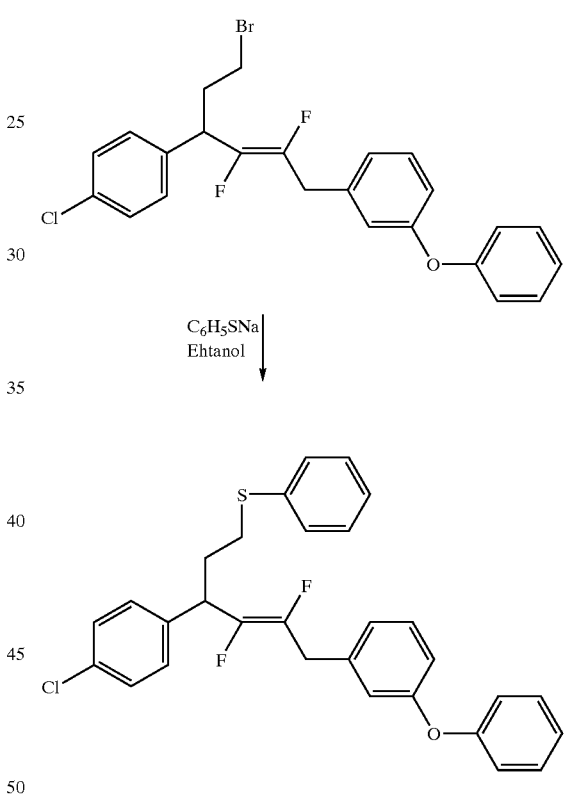

To a stirred solution of 1-[(2E)-6-bromo-4-(4-chlorophenyl)-2,3-difluoro-2-hexenyl]-3-phenoxybenzene (0.308 g, 0.64 mmol) in ethanol (9.6 ml) under nitrogen was added sodium thiophenoxide (0.253 g, 1.91 mmol) and the resulting mixture was stirred at room temperature for two hours. The reaction mixture was concentrated in vacuo, diluted with water (25 ml) and extracted with methylene chloride (3×25 ml). The combined organic extracts were washed with water (2×25 ml), dried over anhydrous sodium sulfate and concentrated in vacuo to a colorless oil (0.187 g). Chromatography on a preparative thin layer silica gel plate eluting with ethyl acetate:hexane (5:95) afforded the title compound as a colorless oil (0.176 g) which was characterized by IR, $^1$HNMR and mass spectral analysis.

EXAMPLE 16

Preparation of (4E)-3-(4-chlorophenyl)-4,5-difluoro-6-(3-phenoxyphenyl)-4-hexenyl phenyl sulfoxide

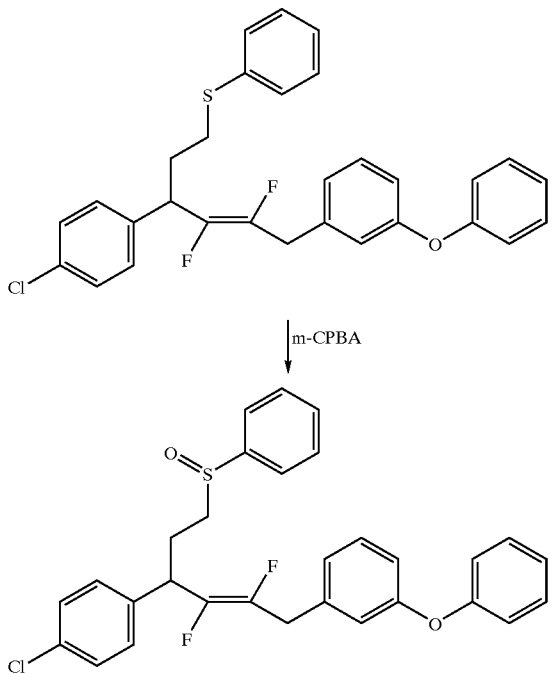

To a stirred solution of 1-[(2E)-4-(4-chlorophenyl)-2,3-difluoro-6-(phenylsulfanyl)-2-hexenyl]-3-phenoxybenzene (0.311 g, 0.61 mmol) in methylene chloride (13 ml) under nitrogen was added dropwise a solution of m-chloroperbenzoic acid (m-CPBA; 0.13 g, 0.65 mmol) in methylene chloride (2 ml) over one minute. The reaction mixture was stirred at room temperature for two hours, diluted with methylene chloride (50 ml) and washed successively with saturated aqueous sodium bicarbonate and water. The organic solution was dried over anhydrous sodium sulfate and concentrated in vacuo to afford the title compound as a colorless syrup (0.318 g), which was characterized by IR, $^1$HNMR, $^{19}$FNMR and mass spectral analysis, and used without further purification.

EXAMPLE 17

Preparation of 1-[(2E)-4-(4-chlorophenyl)-2,3-difluoro-2,5-hexadienyl]-3-phenoxybenzene

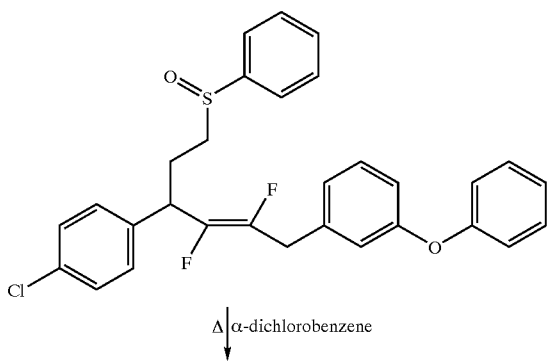

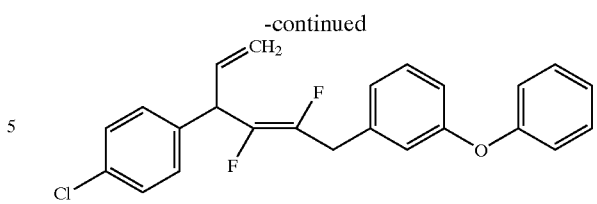

A solution of (4E)-3-(4-chlorophenyl)-4,5-difluoro-6-(3-phenoxyphenyl)-4-hexenyl phenyl sulfoxide (0.318 g, 0.60 mmol) in o-dichlorobenzene (2.4 ml) under nitrogen was heated at 165° C. for 4.5 hours. The solution was cooled to 100° C. and the solvent removed in vacuo. The residue was chromatographed on a preparative thin layer silica gel plate eluting with ethyl acetate:hexane (5:95) to yield the title compound as a pale yellow oil (0.142 g) which was characterized by IR, $^1$HNMR and mass spectral analysis.

Insecticidal and Acaricidal Evaluation of Test Compounds

Test solutions are prepared by dissolving the test compound in a 35% acetone in water mixture to give a concentration of 10000 ppm. Subsequent dilutions are made with water as needed.

*Spodoptera eridania,* 3rd instar larvae, southern armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. After 5 days, observations are made of mortality, reduced feeding, or any interference with normal molting.

*Diabrotica virgifera* virgifera Leconte, 3rd instar western corn rootworm (WCR)

One ccm of fine talc is placed in a 30 ml wide-mouth screw-top glass jar. One ml of the appropriate acetone test solution is pipetted onto the talc so as to provide 1.25 mg of active ingredient per jar. The jars are set under a gentle air flow until the acetone is evaporated. The dried talc is loosened, 1 ccm of millet seed is added to serve as food for the insects and 25 ml of moist soil is added to each jar. The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

*Heliothis virenscens,* 3rd instar tobacco budworm (TBW)

Cotton cotyledons are dipped in the test solution and allowed to dry in a hood. When dry, each is cut into quarters and ten sections are placed individually in 30 ml plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Aphis fabae,* mixed instar, bean aphid (BA)

Pots containing single nasturtium plants (Tropaeolum sp.) about 5 cm tall are infested with about 100–200 aphids one day before the test. Each pot is sprayed with the test solution for 2 revolutions of a 4 rounds per minute (rpm) turntable in a hood. The spray is directed to give complete coverage of the plants and aphids. The sprayed pots are set on their sides on white trays and held for 2 days, following which mortality estimates are made.

*Tetranychus urticae* (OP-resistant strain), 2-spotted spider mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. By the size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made. The tests are rated according to the Bcale shown below and the data obtained are shown in Table I.

Compounds employed in the above-described evaluations are given a compound number and identified by name. Data in Table I are reported by compound number.

| Rating Scale | |
| --- | --- |
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

COMPOUNDS EVALUATED AS INSECTICIDAL AND ACARICIDAL AGENTS

| Number | Compound |
| --- | --- |
| 1 | 1-[(2E)-4-(4-chlorophenyl)-2,3-difluoro-6-methoxy-2-hexenyl]-3-phenoxybenzene |
| 2 | 1[(2E)-4-(4-chlorophenyl)-2,3-difluoro-2,6-heptadienyl]-3-phenoxybenzene |
| 3 | 1-[(2E)-4-(4-chlorophenyl)-2,3-difluoro-2,5-hexadienyl]-3-phenoxybenzene |
| 4 | 4-[(2E)-4-(4-chlorophenyl)-2,3-difluoro-6-methoxy-2-hexenyl]-1-fluoro-2-phenoxybenzene |

TABLE I

Insecticidal And Acaricidal Evaluations

| Compound Number | SAW (100 ppm) | WCR (50 ppm) | TBW (100 ppm) | BA (100 ppm) | TSM (100 ppm) |
| --- | --- | --- | --- | --- | --- |
| 1 | 9 | 8 | 0 | 2 | 0 |
| 2 | 9 | 9 | 9 | 9 | 0 |
| 3 | 9 | 9 | 9 | 9 | 0 |
| 4 | 9 | 9 | 9 | 0 | 0 |

What is claimed is:
1. Compounds of formula I

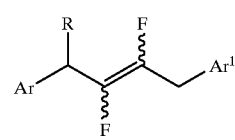

wherein
  Ar is
    phenyl which is unsubstituted or substituted with any combination of from one to three halogen, $C_1$–$C_4$-alkyl, $C_1$–$C_4$-haloalkyl, $C_1$–$C_4$-alkoxy, $C_1$–$C_4$-haloalkoxy or hydroxy groups,
    1- or 2-naphthyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, or
    a 5- or 6-membered heteroaromatic ring containing one to four nitrogen atoms or one to three nitrogen atoms and one sulfur atom or oxygen atom or one or two sulfur and/or oxygen atoms which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;
  R is $C_2$–$C_6$-alkenyl, $C_4$–$C_6$-cycloalkenyl or $C_1$–$C_2$-alkoxy-$C_2$–$C_6$alkyl;
  $Ar^1$ is
    phenoxyphenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups,
    phenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    biphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    phenoxypyridyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    benzylpyridyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    benzylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    benzoylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups,
    1- or 2-naphthyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, or
    a 5- or 6-membered heteroaromatic ring containing one to four nitrogen atoms or one to three nitrogen atoms and one sulfur atom or oxygen atom or one or two sulfur and/or oxygen atoms which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups, and the optical isomers thereof, and the (E)- and (Z)-isomers thereof.

2. Compounds of formula I according to claim 1 wherein

Ar is phenyl which is unsubstituted or substituted with any combination of from one to three halogen, $C_1$–$C_4$-alkyl, $C_1$–$C_4$-haloalkyl, $C_1$–$C_4$-alkoxy or $C_1$–$C_4$-haloalkoxy groups;

R is $C_2$–$C_4$-alkenyl or $C_1$–$C_2$-alkoxy-$C_2$–$C_4$-alkyl; and $Ar^1$ is
- 3-phenoxyphenyl which is unsubstituted or substituted with any combination of from one to six halogen, $C_1$–$C_4$-alkyl, $C_1$–$C_4$-haloalkyl, $C_1$–$C_4$-alkoxy or $C_1$–$C_4$-haloalkoxy groups,
- 3-biphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups, or
- 3-benzylphenyl which is unsubstituted or substituted with any combination of from one to five halogen, $C_1$–$C_4$-alkyl, $C_1$–$C_4$-haloalkyl, $C_1$–$C_4$-alkoxy or $C_1$–$C_4$-haloalkoxy groups.

3. A process for the preparation of a compound of formula I

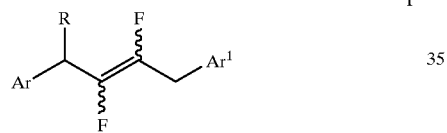

wherein Ar, $Ar^1$, and R are as defined in claim 1 or 2, which process comprises the following steps:

a) reacting a compound of formula II.1

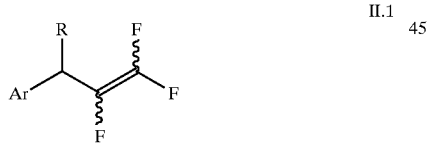

with a defluorinating agent to obtain a compound of formula II.2, and

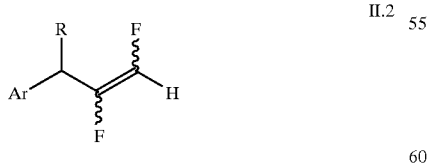

b) reacting the compound of formula II.2 with an alkyllithium base, zinc chloride, tetrakis(triphenylphosphine)palladium(0) and a substituted methyl halide $ZCH_2Ar^1$, wherein Z is chlorine, bromine, or iodine and $Ar^1$ is as defined in claim 1 or 2, to obtain the compound of formula I.

4. A process for the preparation of a compound of formula Ia

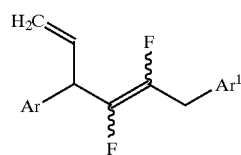

wherein Ar and $Ar^1$ are as defined in claim 1 or 2, which process comprises the following steps:

a) reacting a 2-methoxyethyl compound of formula Ib

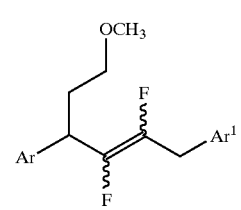

with a demethylating agent to obtain an alcohol of formula III.1

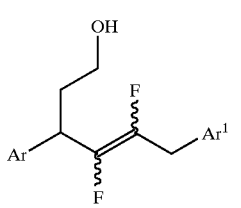

b) reacting the alcohol of formula III.1 with a brominating agent to obtain a bromide of formula V

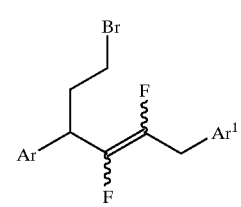

c) reacting the bromide of formula V with a salt of thiophenol in a solvent to obtain a thioether of formula III.2

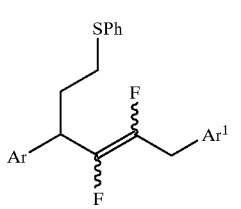

d) reacting the thioether of formula III.2 with an oxidizing agent to obtain a sulfoxide of formula III.3, and

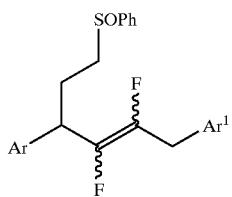

III.3 e) heating the sulfoxide of formula III.3 in a solvent to obtain the compound of formula Ia, wherein in formulae III.1 to III.3 and V, Ar and Ar¹ are defined as in claim 1 or 2.

5. A process for the preparation of a compound of formula Ic

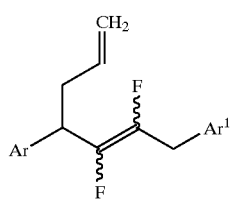

Ic wherein Ar and Ar¹ are as defined in claim 1, which process comprises the following steps:

a) reacting an alcohol of formula III.1

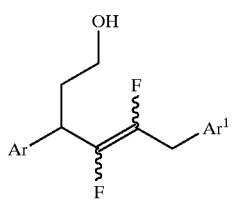

III.1 with an oxidizing agent to obtain an aldehyde of formula III.4

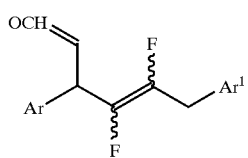

III.4 b) reacting the aldehyde of formula III.4 with a silylating agent to obtain a compound of formula III.5, and

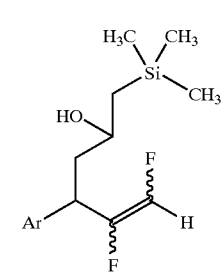

III.5 c) reacting the compound of formula III.5 with an acid to obtain the compound of formula Ic.

6. Intermediates of formula II.A

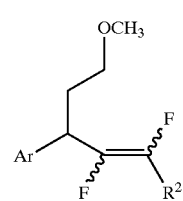

II.A wherein Ar is defined as in claim 1 or 2, and R² is hydrogen or fluorine.

7. Intermediates of formula III

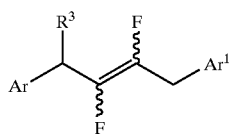

III wherein

Ar and Ar¹ are defined as in claim 1 or 2 and

R³ is phenylthio-$C_2$–$C_6$-alkyl, phenylsulfinyl-$C_2$–$C_6$-alkyl, hydroxy-$C_2$–$C_6$-alkyl, formyl-$C_2$–$C_5$-alkyl, or $C_2$–$C_6$-alkyl vicinally substituted with hydroxy and trimethylsilyl, and the optical isomers thereof, and the (E)- and (Z)-isomers thereof.

8. A method for controlling insect or acarid pests which comprises contacting the pests or their food supply, habitat or breeding grounds with a pesticidally effective amount of a compound of formula I as defined in claim 1.

9. A composition for the control of insect or acarid pests which comprises an agronomically acceptable carrier and a pesticidally effective amount of a compound of formula I as defined in claim 1.

* * * * *